United States Patent
Li

(10) Patent No.: US 8,658,990 B2
(45) Date of Patent: Feb. 25, 2014

(54) RADIATION DOSIMETERS FOR QUANTIFYING THE DOSE OF RADIATION APPLIED DURING RADIATION THERAPY

(75) Inventor: Hui Li, Fenton, MO (US)

(73) Assignee: Washington University, St. Louis, MO (US)

( * ) Notice: Subject to any disclaimer, the term of this patent is extended or adjusted under 35 U.S.C. 154(b) by 309 days.

(21) Appl. No.: 13/320,134

(22) PCT Filed: May 12, 2010

(86) PCT No.: PCT/US2010/034552
§ 371 (c)(1),
(2), (4) Date: Nov. 22, 2011

(87) PCT Pub. No.: WO2010/132569
PCT Pub. Date: Nov. 18, 2010

(65) Prior Publication Data
US 2012/0068084 A1    Mar. 22, 2012

Related U.S. Application Data

(60) Provisional application No. 61/177,822, filed on May 13, 2009.

(51) Int. Cl.
| | | |
|---|---|---|
| G01J 1/58 | (2006.01) |
| G01N 21/63 | (2006.01) |
| G01N 21/64 | (2006.01) |
| G01T 1/00 | (2006.01) |
| G01T 1/02 | (2006.01) |
| G01T 1/10 | (2006.01) |

(52) U.S. Cl.
USPC ............. 250/484.4; 250/483.1; 250/484.3; 250/484.5; 250/484.2; 250/473.1; 250/486.1

(58) Field of Classification Search
USPC ............. 378/62; 252/301.4 R, 301.16; 250/473.1, 484.2, 484.4, 484.5, 337, 250/486.1, 484.1, 483.1; 430/139
See application file for complete search history.

(56) References Cited

U.S. PATENT DOCUMENTS

| | | | | |
|---|---|---|---|---|
| 5,874,744 A | * | 2/1999 | Goodman et al. | 250/584 |
| 2004/0135098 A1 | * | 7/2004 | Katagiri | 250/484.5 |
| 2011/0017925 A1 | * | 1/2011 | Okamura et al. | 250/484.2 |

OTHER PUBLICATIONS

Melendrez et al., "Dosimetric properties of KCl:Eu2+ under alpha, beta, gama, x ray, and ultraviolet irradiation," Appl. Phys. Lett. 68 (24), Jun. 10, 1996, pp. 3398-3340. Retrieved from the internet [Nov. 17, 2013]; Retrieved from url <http://scitation.aip.org/content/aip/journal/apl/68/24/10.1063/1.116516>.*

Nanto et al., "Two-dimensional x-ray sensor utilizing photostimulated luminescence in europium-doped potassium chloride single crystals," SPIE vol. 1736 X-Ray Detector Physics and Applications, 1992, pp. 10-20. Retrieved from the internet [Nov. 17, 2013]; Retrieved from url <http://proceedings.spiedigitallibrary.org>.*

(Continued)

Primary Examiner — David Porta
Assistant Examiner — Yara Green
(74) Attorney, Agent, or Firm — Armstrong Teasdale LLP

(57) ABSTRACT

Radiation dosimeters containing thin $KCl:Eu^{2+}$ storage phosphors for quantifying and/or verifying the dose of radiation applied during radiation therapy. Methods for measuring the amount of radiation applied from a source of radiation and methods for treating a patient having a cancerous tumor are also provided.

20 Claims, 20 Drawing Sheets

(56) References Cited

OTHER PUBLICATIONS

Leblans, "A new needle-crystallline computed radiography detector", J. Digit., 2000, pp. 117-120, vol. 13.

Li et al., "Tape casting of storage phosphor BaFBr:Eu2 + for x-ray imaging", Mater. Sci. Eng. B., 2002, pp. 313-319, vol. 96.

Nanto et al., "Laser-stimulable Transparent KCl:Eu crystals for erasable and rewritable optical memory utilizing photostimulated luminescence", J. Appl. Phys, 1993, pp. 1445-1447, vol. 74.

Nanto et al., "Eu-doped KCl phosphor crystals as a storage material for twodimensional ultraviolet-ray or x-ray imaging sensors", J. Appl. Phys., 1994, pp. 7493-7497, vol. 75.

Nanto et al., New photostimulable phosphor materials for digital radiography:, IEEE Transactions on Nuclear Science, 2000, pp. 1620-1624, vol. 47.

Palm et al., "Predicting energy response of radiographic film in a 6 MV x-ray beam using Monte Carlo calculated fluence spectra and adsorbed dose", Med. Phys., 2004, pp. 3168-3178, vol. 31.

Palm et al., "Influence of phantom material and phantom size radiographic film response in therapy photon beams", Med. Phys., 2005, pp. 2434-2442, vol. 32.

Schmitt et al., "Structured alkali halides for medical applications", Nucl. Insstr. Meth. Phys. Res. B., 2002, pp. 800-804, vol. 191.

Zimmerman et al., "Influence of Li-codoping on the radiation hardness of CsBr:Eu2+", J. Appl. Phys., 2007, pp. 113-117, vol. 101.

* cited by examiner

US 8,658,990 B2

RADIATION DOSIMETERS FOR QUANTIFYING THE DOSE OF RADIATION APPLIED DURING RADIATION THERAPY

CROSS-REFERENHCE TO RELATED APPLICATION

This application is a 35 U.S.C. §371 national stage application of PCT/US 2010/034552, filed May 12, 2010, which claims the benefit of U.S. Provisional No. 61/177,822, filed May 13, 2009, the entireties of which are hereby incorporated by reference for all purposes.

STATEMENT REGARDING FEDERALLY SPONSORED RESEARCH & DEVELOPMENT

This invention was made with government support under grant R21 CA131690, awarded by the U.S. National Institutes of Health. The government has certain rights in the invention

BACKGROUND

The field of the disclosure relates to radiation dosimeters for measuring the amount of radiation applied from a source of radiation during radiation therapy and, particularly, to dosimeters containing europium-doped potassium chloride. Other aspects of the disclosure include methods for measuring radiation from a source and methods for treating a patient having a cancerous tumor.

Radiation oncology (synonymously "radiation therapy") has proven to be an effective method of treating cancerous tumors. Generally, radiation oncology involves the application of precise doses of radiation to a tumorous site. The radiation damages the DNA of the tumor causing it to die or reproduce more slowly. The rate of destruction of the tumor is dependent on the dose absorbed by the tissue.

Radiation dosimetry is a type of quality assurance for radiation therapy treatment. Radiation dosimetry may be utilized to measure or calculate the absorbed dose, to verify the dose of radiation and/or to calibrate the equipment providing the source of radiation.

Conventionally, radiation dosimetry utilized in radiation therapy techniques involves radiographic film such as silver bromide or involves ionization chambers which generate a signal in response to detecting radiation. The use of ionization chambers is limited as they cannot practically be used for multidimensional dose mapping. Radiographic film is a single use detector and cannot reliably be calibrated. Quantitative dosimetry with radiographic film requires the acquisition of a sensitometric curve each time a dosimetric measurement is made. This practice is unreliable as it is based on the assumptions individual films from a single batch and individual pixels on the same sheet share a common response and that the processor performance does not change from film to film. Further, the availability of film and film processors has become limited as radiation oncology clinics move toward digital imaging. A need exists for a quantitative, reusable, high-resolution multidimensional dosimeter that may be utilized for radiation therapy quality assurance.

SUMMARY

One aspect of the present disclosure is directed to a radiation dosimeter for measuring the dose of radiation applied during radiation therapy. The dosimeter includes a storage phosphor. The storage phosphor has a europium-doped potassium chloride active layer with an effective thickness of less than about 10 μm.

Another aspect of the present disclosure is directed to a method for measuring the amount of radiation applied from a source of radiation. A dose of radiation is applied in the direction of a dosimeter comprising a storage phosphor. The storage phosphor has a europium-doped potassium chloride active layer with an effective thickness of less than about 10 μm. The storage phosphor is optically stimulated to emit photons. The emitted photons are detected and a signal is generated based on the amount of photons detected.

Yet another aspect of the present disclosure is directed to a method for treating a patient having a cancerous tumor. A targeted dose of radiation is applied to the cancerous tumor. The targeted dose of radiation that was applied to the tumor is verified by applying a dose of radiation in the direction of a dosimeter comprising a storage phosphor. The storage phosphor has a europium-doped potassium chloride active layer with an effective thickness of less than about 10 μm.

Various refinements exist of the features noted in relation to the above-mentioned aspects of the present disclosure. Further features may also be incorporated in the above-mentioned aspects of the present disclosure as well. These refinements and additional features may exist individually or in any combination. For instance, various features discussed below in relation to any of the illustrated embodiments of the present disclosure may be incorporated into any of the above-described aspects of the present disclosure, alone or in any combination.

BRIEF DESCRIPTION OF THE DRAWINGS

Corresponding reference characters indicate corresponding parts throughout the drawings.

DETAILED DESCRIPTION

Figure 1:
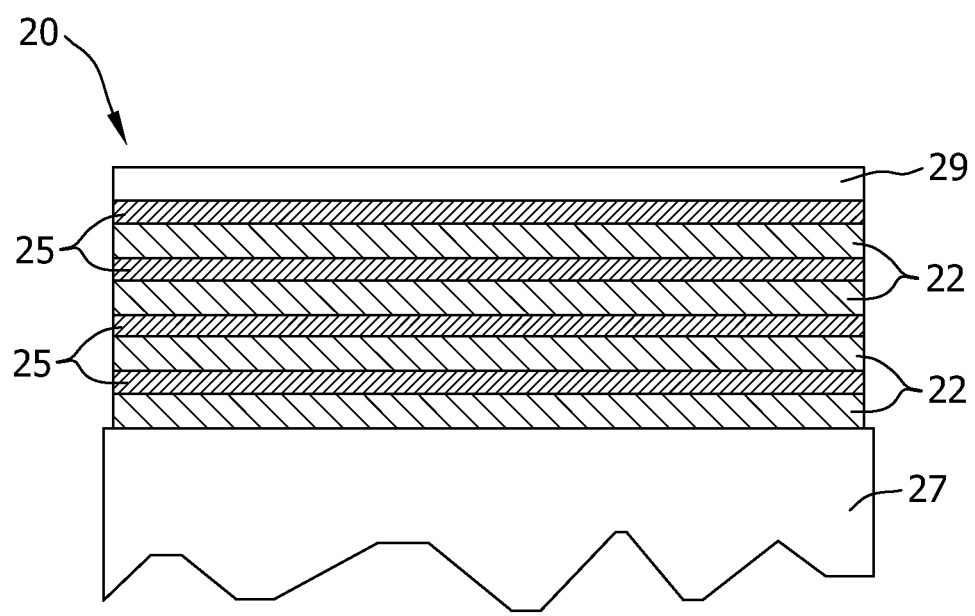
FIG. 1 is a cross-sectional schematic view of a $KCl:Eu^{2+}$ storage phosphor of one embodiment of the present disclosure.

Provisions of the present disclosure relate to radiation dosimeters that include a storage phosphor having a KCl:Eu$^{2+}$ active layer with a thickness less than about 10 µm. Other provisions include methods for measuring the amount of radiation applied from a source of radiation and methods for treating a patient having a cancerous tumor that utilize a storage phosphor having a KCl:Eu$^{2+}$ active layer with a thickness less than about 10 µm.

The KCl:Eu$^{2+}$-based dosimeters of the present disclosure have been found to be a useful material for tissue equivalent radiation dosimetry, in part, because the material is characterized by a relatively small effective atomic number of 18. As described more fully in the Examples, KCl:Eu$^{2+}$-based dosimeters are characterized by a satisfactory radiation hardness. There is no significant change in the stimulation spectra after irradiation up to about 200 Gy when compared to a fresh dosimeter, indicating that, in some embodiments, the storage phosphor could be reused at least about 100 times at about 2 Gy per use (i.e., 200 Gy accumulated). KCl:Eu$^{2+}$-based dosimeters are characterized by a linear response to dose after irradiation from about 0 cGy to about 250 cGy and a supra-linear response thereafter to about 800 cGy. After x-ray irradiation, the photostimulated luminescence signal fades with time and eventually reaches a plateau (about 0.1% per hour) after about 12 hours. This effect might partially be caused by ambient moisture as KCl is generally hygroscopic. It is believed that a relatively thick protective layer on top of the KCl:Eu$^{2+}$ active layer would minimize signal fading. The sensitivity of the dosimeter is independent of the dose rate ranging from about 15 cGy/min (underneath a multileaf collimator) to about 1000 cGy/min. The sensitivity is not energy dependent for either open x-ray or megavoltage electron fields. Over-response to low-energy scattered photons of the dosimeter (e.g., a 1 mm thick point dosimeter described below) is comparable to radiographic film (e.g., Kodak EDR2 film). By sandwiching dosimeters between low-energy photon filters (about 0.3 mm-thick lead foils) during irradiation, the over-response may be minimized.

Based on Monte Carlo simulations, KCl:Eu$^{2+}$-based multidimensional dosimeters with a thickness less than about 10 µm are believed to be characterized by a significantly lower energy dependence relative to radiographic film and are believed to have an overall dose response close to water. It is believed that the dosimeters provide sufficient signal strength in clinical dose ranges due to the intrinsic low background noise associated with storage phosphor techniques. The 1 mm phosphors of Example 1 below are known to provide a signal-to-noise ratio of greater than 5 after irradiation of 0.2 cGy. Theoretical calculations indicate that more than 10,000 photoelectrons may be generated by a dose of 1 cGy in one pixel (0.5 mm×0.5 mm) of a KCl:Eu$^{2+}$-based planar dosimeter with a thickness less than about 10 µm and, particularly, a thickness of about 1 µm.

Monte Carlo dose profile simulations described in Example 13 below illustrate that material less than about 10 µm is highly accurate with a dose response close to water thus allowing the material to be utilized as a minimal energy dependent, high-resolution, reusable dosimeter suitable for, for example, two dimensional megavoltage beam commissioning and dosimetry.

Dosimeters Containing a KCl:Eu$^{2+}$ Storage Phosphor

In one embodiment of the present disclosure, a radiation dosimeter includes a storage phosphor having a europium-doped potassium chloride (KCl:Eu$^{2+}$) active layer with the thickness of the active layer being less than about 10 µm (and in addition or alternatively having an "effective" thickness less than about 10 µm as more fully described below). It is believed that KCl:Eu$^{2+}$ dosimeters store dose information in the form of trapped electrons and holes formed during ionizing radiation. Readout of the dose information may be achieved by liberating the trapped electrons that subsequently migrate to recombination centers (Eu) where they recombine with holes under the emission of photons. Dose information may be read out repeatedly over multiple stimulations. For purposes of the present disclosure, "active layer" refers to a continuous portion of the dosimeter or storage phosphor which responds to x-ray radiation, i.e., which is capable of creating trapped electrons and/or holes upon stimulation with x-ray photon energy. Storage phosphors of embodiments of the present disclosure may contain more than one active layer without departing from the scope of the present disclosure.

KCl:Eu$^{2+}$-based dosimeters of embodiments of the present disclosure may be characterized by improved radiation hardness. As described in Example 7, the crystal lattice of the dosimeter stayed nearly intact after an irradiation to 200 Gy (FIG. 9), indicating that this material could be reused many times. In one embodiment of the present disclosure, the KCl:Eu$^{2+}$-based dosimeter is capable of being reused in radiation dose quality assurance at least about 25 times at a radiation dose of about 2 Gy (about 50 Gy accumulated dose). In other embodiments, the dosimeter is capable of being reused in radiation dose quality assurance at least about 50 times (about 100 Gy accumulated), at least about 75 times (about 150 Gy accumulated) or even at least about 100 times at a radiation dose of about 2 Gy (about 200 Gy accumulated). In one embodiment, the KCl:Eu$^{2+}$ storage phosphor loses less than about 25% of its sensitivity after an accumulated dose of about 200 Gy and, in other embodiments, loses less than about 20% or even loses less than about 17% of its sensitivity after an accumulated dose of about 200 Gy.

In one embodiment, the KCl:Eu$^{2+}$ storage phosphor is doped with lithium ions as described by Zimmermann et al. in "Influence of Li-codoping on the radiation hardness of CsBr:Eu$^{2-}$," J. Appl. Phys., 101, 113711 (2007), which is incorporated herein for all relevant and consistent purposes. It is believed that lithium ions suppress generation of M-centers during x-ray irradiation resulting in improved radiation resistance.

As described in Example 13 below, it is believed that KCl:$Eu^{2+}$ storage phosphors having an active layer with a thickness (and in addition or alternatively "effective" thickness) of less than about 10 μm create a more water-like response for the dosimeter. In various embodiments, the thickness of the active layer may be less than about 10 μm, less than about 5 μm, less than about 3 μm or even less than about 1 μm. In other embodiments, the thickness of the active layer may be from about 0.05 μm to about 10 μm, from about 0.05 μm to about 5 μm, from about 0.05 μm to about 1 μm or from about 0.1 μm to about 1 μm. For purposes of the present disclosure, "thickness" of the KCl:$Eu^{2+}$ storage phosphor refers to the thickness of material containing KCl:$Eu^{2+}$ crystals and does not refer to a substrate, buffer or protective layers.

The amount of europium in the KCl:$Eu^{2+}$-based dosimeter may be at least about 50 ppm by weight, at least about 100 ppm, at least about 300 ppm or even at least about 450 ppm. In various other embodiments, the amount of europium in the KCl:$Eu^{2+}$ storage phosphor is from about 50 ppm to about 750 ppm, from about 300 ppm to about 650 ppm or from about 50 ppm to about 150 ppm.

KCl:$Eu^{2+}$ storage phosphors may generally be made according to any method known in the art. KCl:$Eu^{2+}$ crystals may be made by the Bridgman method in which a solid-liquid interface is maintained. In order to achieve a KCl:$Eu^{2+}$ crystal thickness less than about 10 μm, a physical vapor deposition (PVD) method may be utilized. For instance, tape casting may be employed as described by Li et al. in "Tape casting of storage phosphor BaFBr:$Eu^{2+}$ for x-ray imaging," in Mater. Sci. Eng. B., 96, 313-319 (2002), which is incorporated herein for all relevant and consistent purposes. In one embodiment, vacuum evaporation is employed as described by P. Leblans in "A new needle-crystalline computed radiography detector," J. Digit., 13, 117-120 (2000) and/or by B. Schmitt et al. in "Structured alkali halides for medical applications," Nucl. Instr. Meth. Phys. Res. B., 191, 800-804 (2002), both of which are incorporated herein for all relevant and consistent purposes. The KCl:$Eu^{2+}$ storage phosphors may be doped with europium by adding a europium containing compound such as, for example, $EuCl_3.6H_2O$, to molten KCl.

KCl:$Eu^{2+}$ storage phosphors according to embodiments of the present disclosure have a single KCl:$Eu^{2+}$ active layer. Alternatively and in one embodiment and as shown in FIG. 1, a KCl:$Eu^{2+}$-storage phosphor may have a layered structure. The storage phosphor 20 may include buffer layers 22 and KCl:$Eu^{2+}$ active layers 25. The buffer layers 22 may be made of transparent materials with a low atomic number (low-Z) and, in one embodiment, are constructed of low-Z polymers. The buffer layers 22 absorb secondary electrons generated by the interaction between low energy scattered photons and the KCl:$Eu^{2+}$ material and prevent the photons from reaching other KCl:$Eu^{2+}$ layers 25. The multilayer storage phosphor 20 exhibits water-like behavior and provides more signals. The thickness of the buffer layers 22 may be less than about 50 μm and, in other embodiments, is less than about 30 μm, from about 5 μm to about 50 μm or from about 10 μm to about 30 μm. In various embodiments, the thickness of the KCl:$Eu^{2+}$ active layers 25 may be less than about 10 μm, less than about 5 μm, less than about 3 μm or even less than about 1 μm. In other embodiments, the thickness of the active layers 25 may be from about 0.05 μm to about 10 μm, from about 0.05 μm to about 5 μm, from about 0.05 μm to about 1 μm or from about 0.1 μm to about 1 μm. The buffer layers 22 and KCl:$Eu^{2+}$ layers 25 may be supported on a substrate 27 and may have a protective layer 29 at the surface of the storage phosphor 20. In one embodiment, the substrate layer is polyethylene terephthalate. While the storage phosphor 20 illustrated in FIG. 1 is shown with four buffer layers 22 and four KCl:$Eu^{2+}$ layers 25, more or less layers may be included without departing from the scope of the present disclosure.

Figure 2:
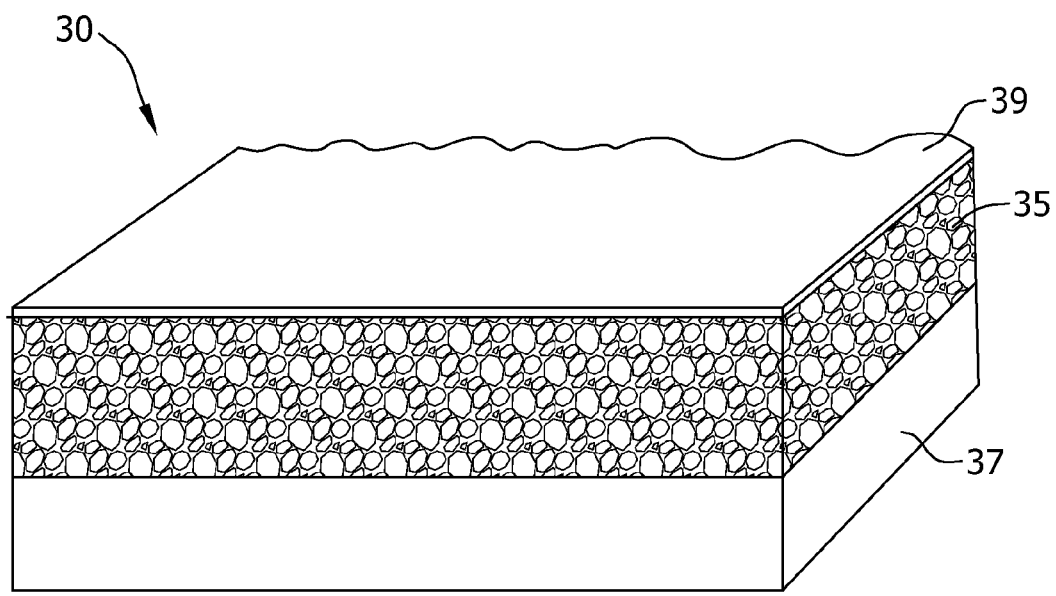
FIG. 2 is a perspective schematic view of a $KCl:Eu^{2+}$ storage phosphor of a second embodiment of the present disclosure.

In another embodiment and as shown in FIG. 2, the storage phosphor 30 includes a substrate 37 (e.g., polyethylene terephthalate), protective layer 39 and active layer 35. The active layer contains an agglomeration of KCl:$Eu^{2+}$ material and binder material. The binder may be a low-Z polymer material. The volume ratio of binder to KCl:$Eu^{2+}$ may be at least about 1:2, at least about 1:1 or at least about 3:1. In one embodiment, the ratio is from about 1:1 to about 5:1. The thickness of the active layer 35 may be at least about 1.5 μm, at least about 5 μm, at least about 10 μm, at least about 20 μm or even at least about 40 μm. In some embodiments, the thickness of the active layer is from about 1.5 μm to about 75 μm, from about 5 μm to about 75 μm, from about 1.5 μm to about 50 μm or from about 5 μm to about 50 μm. The active layer 25 may also be characterized by an "effective" thickness of KCl:$Eu^{2+}$ material. Generally an "effective" thickness is the thickness the active layer would have if it did not contain any binder material. For instance, if the thickness of the active layer 35 is about 16 μm and the volume ratio of binder to KCl:$Eu^{2+}$ is about 3:1, the effective thickness of the active layer 35 is about 4 μm. In various embodiments, the effective thickness of the active layer 35 is less than about 10 μm, less than about 5 μm, less than about 3 μm or even less than about 1 μm. In other embodiments, the effective thickness of the active layer may be from about 0.05 μm to about 10 μm, from about 0.05 μm to about 5 μm, from about 0.05 μm to about 1 μm or from about 0.1 μm to about 1 μm. In embodiments where the storage phosphor does not contain binder material, the effective thickness is equal the thickness of the active layer and the terms "thickness" and "effective thickness" may be used interchangeably.

Figure 3:
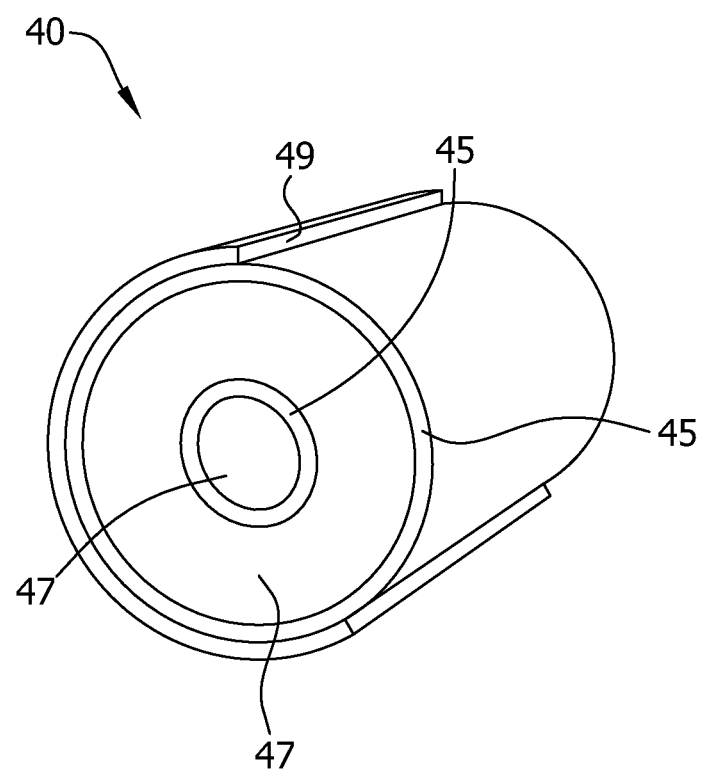
FIG. 3 is a perspective schematic view of a $KCl:Eu^{2+}$ storage phosphor of a third embodiment of the present disclosure.

It should be understood that dosimeter designs other than planer film-like KCl:$Eu^{2+}$ dosimeters may be made with a physical make-up similar to classic computed radiography panels. For example, KCl:$Eu^{2+}$ dosimeters may be manufactured in a cylindrical geometry using, for example, vacuum evaporation. This cylindrical geometry will make it particularly suitable for commissioning and quality assurance of volumetric modulated radiation therapy, intensity modulated arc therapy and helical radiation therapy. An exemplary cylindrical dosimeter is illustrated in FIG. 3. The cylindrical storage phosphor 40 has a layered structure with which includes KCl:$Eu^{2+}$ active layers 45 and phantom layers 47. Phantom layers may be made of low-Z polymers, Solid Water® or other water-equivalent materials. The phosphor 40 may include a protective layer 49 which is shown in FIG. 3 as being partially removed for purposes of illustration.

Methods for Measuring Radiation

The dosimeters and storage phosphors of embodiments of the present disclosure may be utilized in methods for measuring radiation from a radiation source such as radiation applied during radiation therapy. Radiation therapy requires quality assurance of the dose applied by, for example, directly measuring the dose or accumulated dosages, measuring a dose other than the dose applied to the patient for therapy to verify proper functioning of the radiation therapy system and calibration of the radiation therapy system.

In one embodiment, the method includes applying a dose of radiation in the direction of a dosimeter comprising a KCl:$Eu^{2+}$ storage phosphor, the storage phosphor having an active layer with a thickness of less than about 10 μm. The source of x-rays may be a linear accelerator. In various embodiments, the radiation applied may be more than the radiation conventionally applied in radiology. X-ray voltage may be in the orthovoltage or megavoltage ranges. In some embodiments, the x-ray voltage is at least about 0.5 MV or even about 1 MV.

Once the storage phosphor has been irradiated, it may be optically stimulated to emit photons. The phosphor may be stimulated by a focused laser beam (e.g., yellow He—Ne laser) or focused visible light (e.g. a lamp focused with a monochromator). In one embodiment, the storage phosphor is stimulated at a wavelength from about 450 nm to about 700 nm and, in other embodiments, from about 540 nm to about 590 nm or from about 555 nm to about 575 nm. The KCl:Eu$^{2+}$ storage phosphor typically emits a PSL emission spectra with a peak of about 420 nm. Emission spectra may be detected by a spectrofluorometer (e.g., Hitachi F-3010). The intensity of the emission (i.e., the signal) from the storage phosphor may be correlated to a radiation dose. If the correlated radiation dose differs from the dose that was believed to be applied, the dosing system and equipment may be calibrated and corrected to apply the correct dosage. In another embodiment, the signal may be used to verify a radiation dose applied to cancerous tissue of a patient. In another embodiment, the signal may be used to quantify the radiation dose received by a radiation worker, functioning as a radiation safety monitor or film badge.

The dose applied and detected by the storage phosphor for calibration or verification may be the same dose applied to the patient to treat a cancerous tissue or may be a dose that was not applied to a patient and was applied only for purposes of calibration and verification.

As described above, the KCl:Eu$^{2+}$ storage phosphor may be reused many times. To erase or reset the KCl:Eu$^{2+}$ storage phosphor after each use, the phosphor may be illuminated with visible light. In one embodiment of the present disclosure, the storage phosphor is reset and a second dose of radiation is applied in the direction of the dosimeter. The storage phosphor may be optically stimulated to emit photons after the second dose of radiation is applied and a second signal is generated based on the amount of photons detected.

In one embodiment of the present disclosure, the KCl:Eu$^{2+}$-based dosimeter is used in radiation dose quality assurance at least about 25 times at a radiation dose of about 2 Gy (i.e., is reused until a accumulated dose of about 50 Gy is achieved). In other embodiments, the dosimeter is used in radiation dose quality assurance at least about 50 times (about 100 Gy accumulated), at least about 75 times (about 150 Gy accumulated) or even at least about 100 times at a radiation dose of about 2 Gy (about 200 Gy accumulated dose). In one embodiment, the KCl:Eu$^{2-}$ storage phosphor loses less than about 25% of its sensitivity after an accumulated dose of about 200 Gy and, in other embodiments, loses less than about 20% or even loses less than about 17% of its sensitivity after an accumulated dose of about 200 Gy.

In one embodiment of radiation dose quality assurance, characteristic sensitometric curves of the KCl:Eu$^{2-}$-based storage phosphor are predetermined and stored. This allows, for example, the appropriate sensitometric curve to be selected from a stored library for a specific clinical case. Further, when the sensitometric curves are acquired in similar beam and phantom geometries as the measurement dosimeter, the effect of a moderately high Z on the PSL energy dependence of a KCl:Eu$^{2+}$ dosimeter may become clinically insignificant. More importantly, because the dosimeter is reusable, the energy dependence artifact could be reliably rectified using Monte Carlo techniques such as, for example, those developed by Palm et al. in "Predicting energy response of radiographic film in a 6 MV x-ray beam using Monte Carlo calculated fluence spectra and absorbed dose," Med. Phys., 31, 3168-3178 (2004) and Palm et al. in "Influence of phantom material and phantom size on radiographic film response in therapy photon beams," Med. Phys., 32, 2434-2442 (2005), each of which is incorporated herein for all relevant and consistent purposes.

The KCl:Eu$^{2+}$ storage phosphor used for measuring radiation and/or radiation dose quality assurance may have an active layer with a thickness (alternatively or in addition having an effective thickness) of less than about 10 μm. In other embodiments, the active layer has a thickness of less than about 5 μm, of less than about 3 μm or even of less than about 1 μμm. In other embodiments, the thickness of the active layer may be from about 0.05 μm to about 10 μm, from about 0.05 μm to about 5 μm, from about 0.05 μm to about 1 μm or from about 0.1 μm to about 1 μm. In one embodiment, the KCl:Eu$^{2+}$ storage phosphor is doped with lithium ions. The amount of europium in the KCl:Eu$^{2+}$-based dosimeter may be at least about 50 ppm, at least about 100 ppm, at least about 300 ppm or even at least about 450 ppm. In various other embodiments, the amount of europium in the KCl:Eu$^{2+}$ storage phosphor is from about 50 ppm to about 750 ppm, from about 300 ppm to about 650 ppm or from about 50 ppm to about 150 ppm.

Methods for Treating Patients with a Cancerous Tumor

In one aspect of the present disclosure, the KCl:Eu$^{2}$-based storage phosphor is utilized in a method for treating a patient having a cancerous tumor. A targeted dose of radiation is applied to the cancerous tumor according to protocols and dosages known and determinable within the radiation oncology field. The targeted dose of radiation applied to the tumor is verified by applying a dose of radiation in the direction of a dosimeter, the dosimeter including a storage phosphor having a KCl:Eu$^{2+}$ active layer with a thickness of less than about 10 μm.

The dose applied and detected by the storage phosphor may be the same dose applied to the patient to treat a cancerous tissue or may be a dose that was not applied to a patient and was applied only for purposes of calibration and verification. When the dose to be detected by the storage phosphor is the same dose applied to a patient for radiation therapy, the dosimeter may be placed on the patient's skin and may be in the radiation field or outside of the radiation field. The radiation treatment utilized for treatment may be, for example, external beam radiotherapy (2DXRT), external beam radiotherapy (EBRT), 3D conformal radiotherapy (3DCRT) or Intensity-Modulated Radiation Therapy (IMRT). The dosimeter may be utilized in three-dimensional applications by stacking the phosphor plates. The targeted dose of radiation applied in a treatment session may be at least about 0.5 Gy and, in other embodiments, is at least about 1.5 Gy, from about 1.5 to about 3 Gy or from about 1.8 to about 2 Gy. In some embodiments, the total dose of radiation applied to the patient is fractionated meaning a partial dose of radiation is applied many times (e.g., from about 1.5 to about 3 Gy) until the total dose is achieved. The total dose of radiation may be from about 5 Gy to about 80 Gy.

Application of the dose and reading of the dosimeter are generally described above. Generally, the dosimeter may be erased and reused as described. In various embodiments, the KCl:Eu$^{2+}$ storage phosphor has a thickness (and alternatively or in addition has an effective thickness) of less than about 10 μm. In other embodiments, the storage phosphor has a thickness of less than about 5 μm, of less than about 3 μm or even of less than about 1 μm. In other embodiments, the thickness of the active layer may be from about 0.05 μm to about 10 μm, from about 0.05 μm to about 5 μm, from about 0.05 μm to about 1 μm or from about 0.1 μm to about 1 μm. In one embodiment, the KCl:Eu$^{2+}$ storage phosphor is doped with lithium ions. The amount of europium in the KCl:Eu$^{2+}$-based dosimeter may be at least about 50 ppm, at least about 100 ppm, at least about 300 ppm or even at least about 450 ppm. In various other embodiments, the amount of europium in the KCl:Eu$^{2+}$ storage phosphor is from about 50 ppm to about 750 ppm, from about 300 ppm to about 650 ppm or from about 50 ppm to about 150 ppm.

While the embodiments described above have been described with europium being used as the potassium chloride dopant, it should be understood other materials may be used with or substituted for europium. Thallium, terbium, praseodymium and cerium and compounds containing these elements as well as mixtures of the compounds and/or elements may be used as an alternative or in addition to europium. Further in this regard, it should be also understood that other materials may be used with or substituted for KCl such as, for example, KBr which may be used to form a mixed crystal in the form of $KBr_xCl_{1-x}$.

EXAMPLES

Example 1

Production of a Dosimeter Containing KCl:Eu$^{2+}$ and Phantoms

Cylindrical KCl:Eu$^{2+}$ dosimeters 7 mm in diameter and 1 mm thick were fabricated. The polycrystalline KCl:Eu$^{2+}$ storage phosphors were synthesized using a conventional solid state reaction method. The Eu molar concentration of the phosphors was 500 ppm. Raw materials of reagent grade KCl and $EuCl_3 \cdot 6H_2O$ were thoroughly mixed by a planetary ball mill. The mixture was then pressed into discs at an average force of 5 tons for 10 minutes. The discs with 7 mm diameter and 1 mm thickness were sintered at 700° C. using a tube furnace for 3 hours followed by a natural cooling down to 300° C. and a rapid cooling to room temperature.

Figure 4:
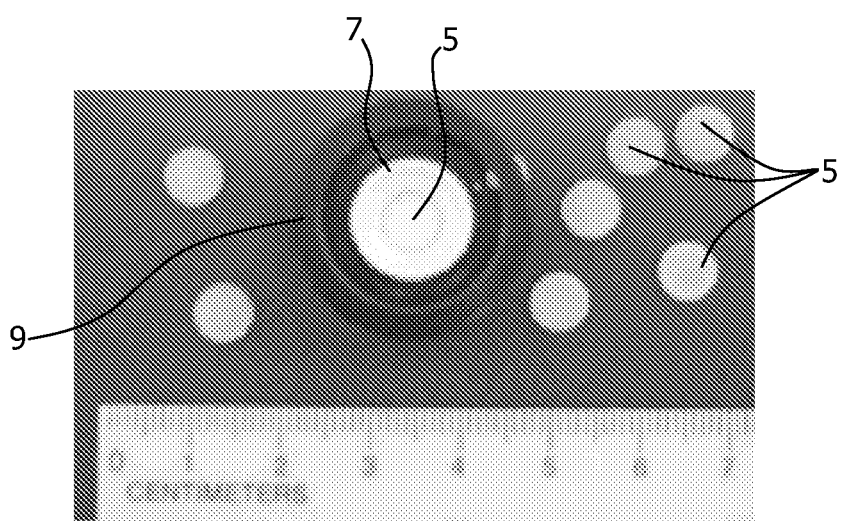
FIG. 4 is a photocopy of a photograph of $KCl:Eu^{2+}$-based dosimeters of one embodiment of the present disclosure and as fabricated according to Example 1.

The cylinders are shown in FIG. 4 and generally referenced as numeral 5. A holder 7 attaches the dosimeters 5 to an integrating sphere 9 during readout. For perspective, the dosimeters 5 are shown with reference to a ruler 10.

A phantom was constructed by stacking 40×40 cm$^2$ SOLID WATER® slabs (SW-457, Gammex RMI, Middleton, Wis.) to a thickness of 30 cm. A linear array of holes 7.5 mm in diameter and 2 mm in depth were machined across the center of a 5 mm thick slab to host the dosimeters during irradiation. Prior to irradiation, the dosimeters were optically bleached ("reset" or "erased") for 5 seconds using a 500 W tungsten-halogen lamp.

Example 2

Irradiation of the Dosimeter

The dosimeters of Example 1 were irradiated by x-ray beams. X-ray beams had nominal energies of 6 MV, 10 MV and 18 MV. Electron beams had nominal energies of 6 MeV, 9 MeV, 12 MeV, 16 MeV and 20 MeV. The beams were generated by a Varian 23EX (Varian Medical Systems, Palo Alto, Calif.) linear accelerator or an Elekta Precise (Elekta, Norcross, Ga.) linear accelerator. The dosimeter plane was oriented perpendicular to the beam central axis for all irradiations. During irradiation, the accelerator output was monitored using a Farmer-type ionization chamber (0.6 cm$^3$) (PTW N23333, Friedberg, Germany) inserted into a 40×40×3 cm$^3$ solid water slab placed 7 cm below the dosimeter plane. The nominal dose rate was 600 MU/minute unless otherwise noted.

Due to the limited availability of the linear accelerators, and to provide consistent experimental conditions, the irradiations were performed during evenings. The irradiated dosimeters were kept in the dark and read on the next day. Each dosimeter was read twice, including removing the dosimeter from the integrating sphere port and remounting. Differences between the two readings were usually less than 1%. Unirradiated dosimeters were also read to provide background signals. Net signals were obtained by subtracting the background.

Before and after each irradiation session, the dosimeters were irradiated to 200 cGy in a large open field in order to determine the relative sensitivity, or "chip factor," of each dosimeter. These two sets of chip factors were usually consistent within 2% for each chip. The averages were used to correct for the sensitivity variation among dosimeters.

Example 3

Read-Out of the Dosimeters

Figure 5:
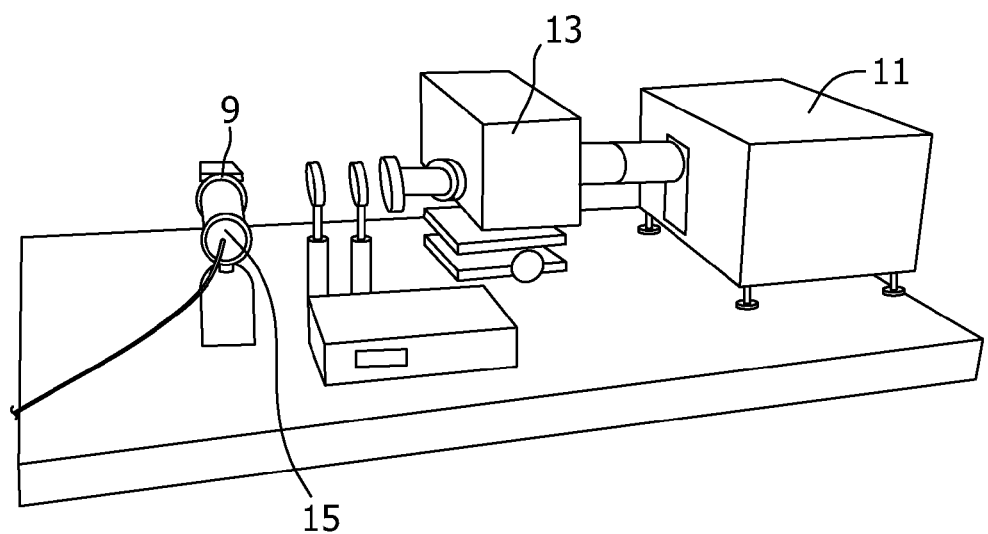
FIG. 5 is a schematic of a photograph of equipment utilized for the readout system of Example 3.

Dosimeters irradiated according to Example 2 were read using the equipment arrangement of FIG. 5 except for photoluminescence stimulation and emission spectra measurements. The stimulation power was supplied by a 100 W quartz tungsten-halogen lamp 11 (Newport, Stratford, Conn.). The stimulation wavelength of 570 nm was selected using a motorized monochromator 13 (Cornerstone 130, Newport) with a grating of 1200 lines/mm. The monochromator 13 had an integrated shutter that was controlled through a GPIB interface and used to switch the stimulation light on and off. The stimulation light was chopped with an optical chopper (Model SR540, Stanford Research System, Sunnyvale, Calif.) set to 80 Hz in order to provide a reference signal to a lock-in amplifier for phase sensitive detection. The stimulation light was focused by a series of lenses and directed to an integrating sphere with multiple ports (LabSphere, North Sutton, N.H.). The KCl:Eu$^{2+}$ dosimeter was attached to an integrating sphere 9 and mounted on a port opposite a photomultiplier tube 15 (PMT, Hamamatsu, Bridgewater, N.J.) which collected and amplified the PSL signals. The gain of the PMT was controlled through a DC power supply (Model PS310, Stanford Research System) that supplied high voltage up to 1.25 kV. Between the integrating sphere and PMT tube was a set of Schott glass bandpass filters, a BG-3 and a BG-39, each 3 mm thick. The filter combination had a maximum sensitivity at 420 nm. The PMT output current was converted into voltage that was measured using a dual-channel lock-in amplifier (Model SR830, Stanford Research System) and recorded on a personal computer. The system was controlled through a GPIB interface. A typical reading involved opening the shutter, waiting 1 second for the signal to stabilize, and then taking 10 consecutive measurements at a time interval of 100 milliseconds. The mean of the 10 measurements was recorded as a reading.

Example 4

Simulation and Emission Spectra of the Dosimeters after Irradiation

The stimulation spectra were obtained by scanning the monochromator 13 between 450 nm and 700 nm in 1 nm increments while the PSL signals were collected through a narrow bandpass filter (FB420-10, Newport). The spectra were then corrected for the diffraction efficiency of the grating and the stimulation power as a function of wavelength, as measured by a calibrated silicone photodiode (Model FDS100-CAL, Thorlabs, Newton, N.J.).

In order to obtain the emission spectrum, a 5 mW, 594 nm yellow He—Ne laser (Melles Griot, Covina, Calif.) was used in place of the halogen lamp for stimulation. The laser power was attenuated so that the photostimulated luminescence (PSL) signal decrease due to continuous stimulation during a typical scan time of 30 seconds was about 10%. The monochromator was placed between the integrating sphere and the PMT, which was fit with a BG-3 and a BG-39 filter (3 mm each). The emission spectrum was obtained by scanning the monochromator from 300 nm to 540 nm with a 0.5 nm step and correcting for signal depletion and spectral response of the PMT.

Figure 6:
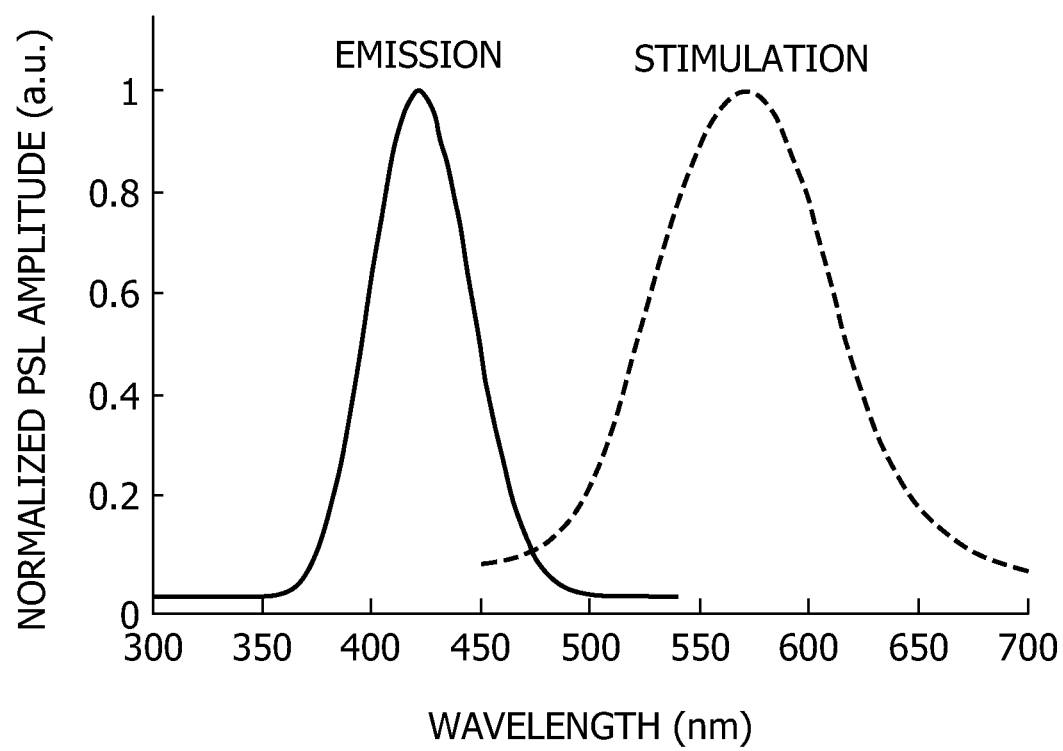
FIG. 6 graphically illustrates the emission and stimulation spectra of the $KCl:Eu^{2+}$-based dosimeters of FIG. 4 after x-ray irradiation.

FIG. 6 shows the emission and stimulation spectra of the KCl:$Eu^{2+}$ dosimeter after x-ray irradiation. The dosimeter emitted intense PSL centered at 420 nm when stimulated with a yellow laser (594 nm). The maximum stimulation efficiency occurred at 570 nm, which was subsequently selected as the readout wavelength.

Example 5

Readout Signal Loss of the Dosimeters

Figure 7:
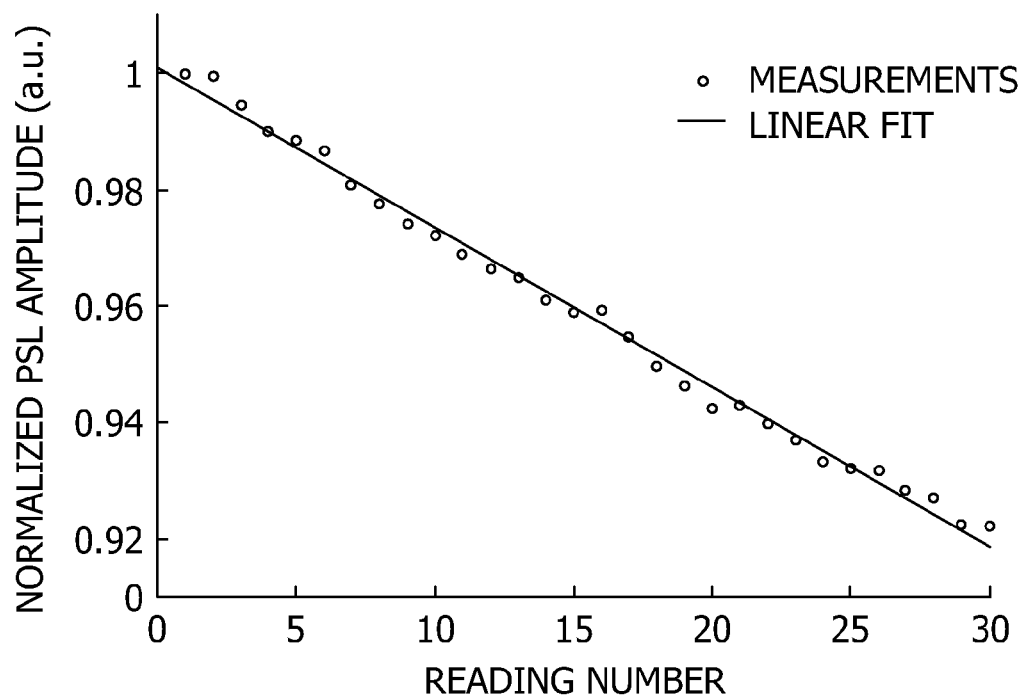
FIG. 7 graphically illustrates the readout signal loss of the dosimeters of FIG. 4 measured over 30 consecutive readings.

FIG. 7 shows the readout signal lost measured over 30 consecutive readings taken at 10 second intervals 13 hours after irradiation. The total read time was about 5 minutes. As shown later, the signal fading was negligible during this 5 minute period. The signal decrease was therefore attributed solely to partial depletion of trapped electrons.

A linear fit of the 30 readings had a slope of −0.0027, indicating that each reading depleted approximately 0.27% of the existing trapped electrons. It should be noted that the stimulation power can be straightforwardly altered by applying gray filters. Therefore, a smaller depletion rate would be readily achieved at the expense of signal strength.

Example 6

Readout Signal Fading of the Dosimeters

KCl:$Eu^{2+}$ dosimeters were irradiated by a dose of 200 cGy and read repeatedly for 24 hours beginning immediately after irradiation. Each reading was corrected for the reading signal depletion as measured above. In general, a fixed time delay between irradiation and readout was used to minimize errors associated with variable signal fading. In order to measure the impact of fading, a batch of 8 dosimeters were exposed to a 6 MV beam up to 400 cGy, and were read at delay times of 20, 44 and 68 hours. The results were normalized to the readings at 100 cGy and compared.

Figure 8:
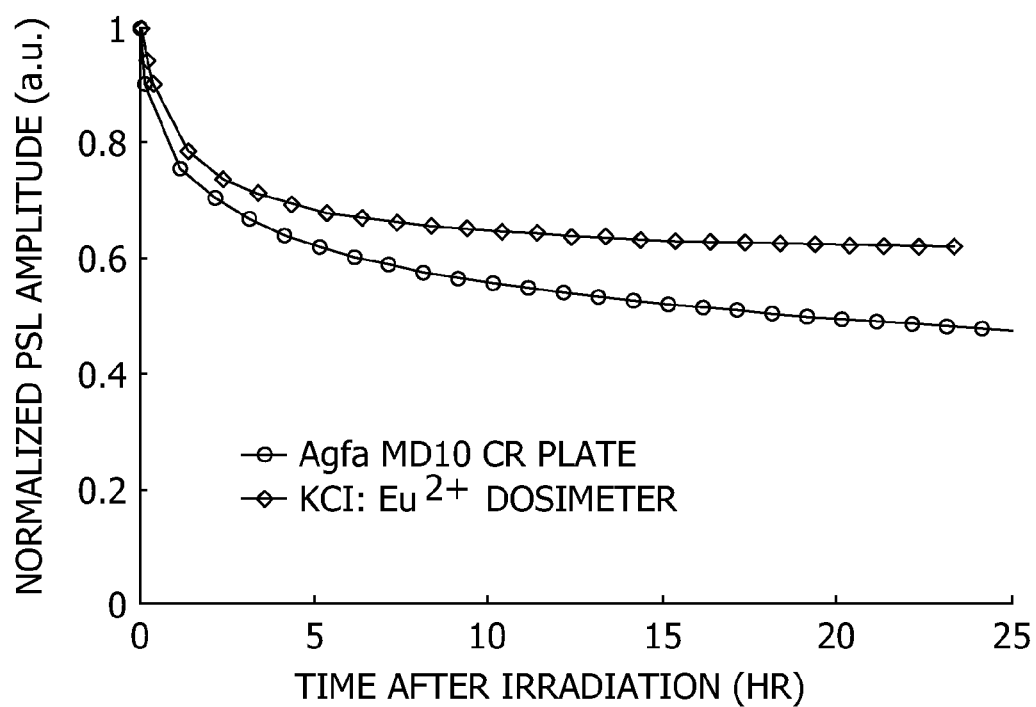
FIG. 8 graphically illustrates the fading characteristics of the $KCl:Eu^{2+}$-based dosimeters of FIG. 4 and an Agfa MD10 CR plate.

FIG. 8 shows the fading characteristics of the prototype KCl:$Eu^{2+}$ dosimeter. The fading curve was corrected for the partial depletion of 0.27% per readout as determined previously. 62% of the original signal remained after 24 hours, and the signal eventually reached a plateau at a slow fading rate of about 0.1% per hour. Compared with an Agfa MD10 CR plate, KCl:$Eu^{2+}$ shows considerably better fading characteristics. Since a fixed delay time of 20 hours between irradiation and reading was used (unless otherwise noted), the uncertainty due to signal fading was estimated to be 0.2% for a typical measurement session of 2 hours.

Example 7

Radiation Hardness of the Dosimeters

Figure 9:
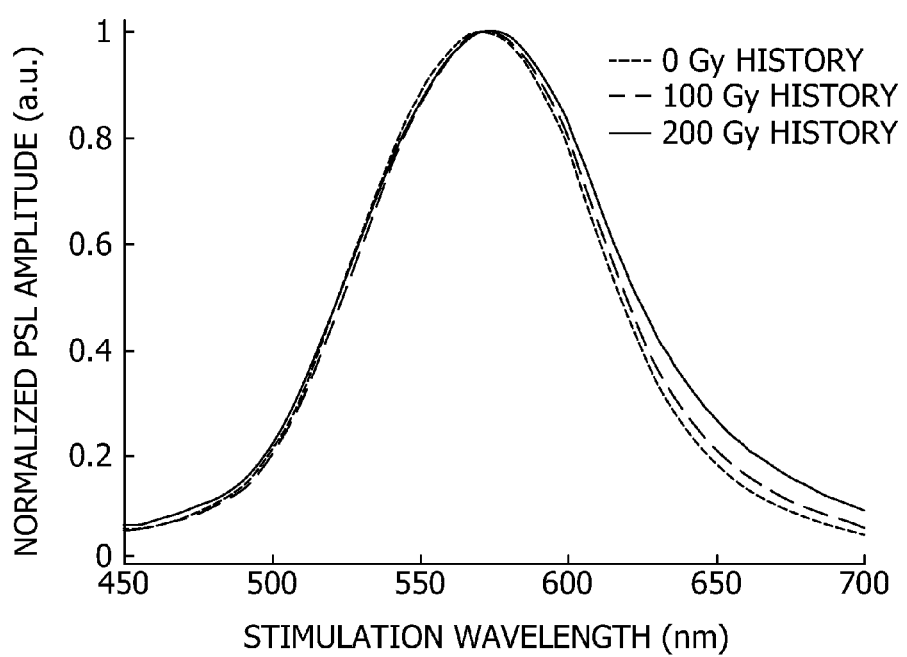
FIG. 9 graphically illustrates stimulation spectra of a fresh dosimeter of FIG. 4 after irradiation to 100 Gy and 200 Gy.

Three dosimeters were first irradiated with 0, 100, and 200 Gy by a 6 MV beam. These dosimeters were subsequently erased, irradiated to 200 cGy, and read. As shown in FIG. 9, there was no significant change in the stimulation spectra after irradiation to 100 Gy and 200 Gy, respectively, compared to a fresh KCl:$Eu^{2+}$ dosimeter. The slight red shift could be caused by the increased creation of M(Cl⁻) centers, the aggregate center of two neighboring chlorine ion vacancies occupied by two electrons. A 15% loss of sensitivity was observed after the dosimeter received an accumulated dose of 200 Gy. This sensitivity loss may be attributed to an agglomeration of $Eu^{2+}$ ions leading to luminescence quenching.

Example 8

Dose Response of the Dosimeters

Figure 10:
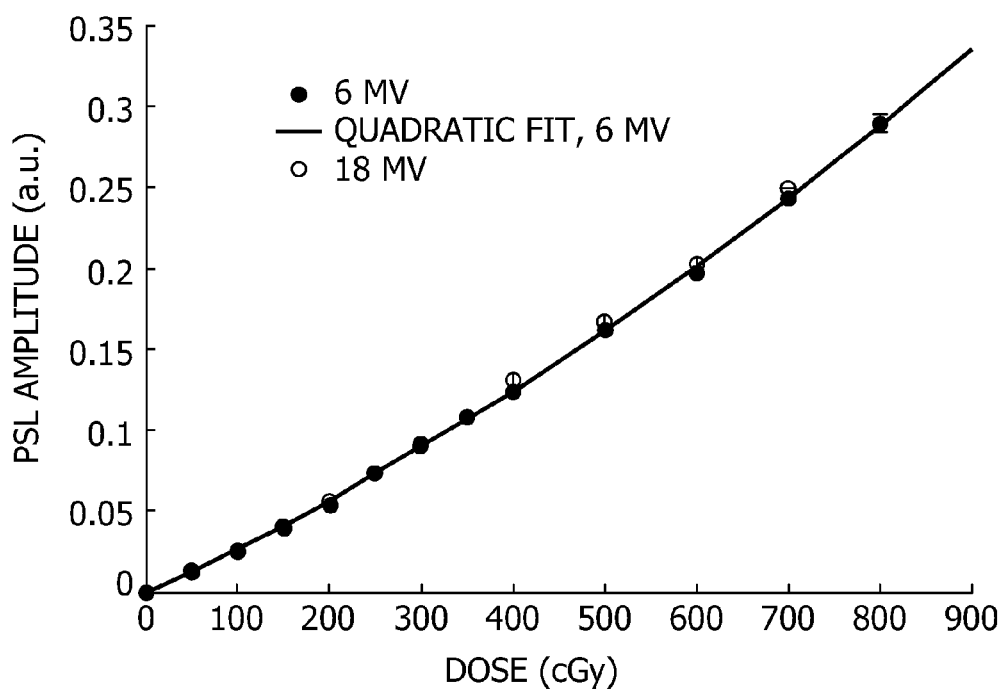
FIG. 10 graphically illustrates the response of the dosimeters of FIG. 4 after an x-ray dose for 6 MV and 18 MV beams.

Twelve dosimeters were irradiated individually up to 800 cGy with a source-skin distance (SSD) of 90 cm, depth of 10 cm and field size of 20×20 $cm^2$ using 6 MV, 10 MV, and 18 MV beams. FIG. 10 shows the dosimeter response for 6 MV and 18 MV beams. The two curves agreed with each other within 2%. Similar to thermoluminescent dosimeters, KCl:$Eu^{2+}$ dosimeters exhibited a supra-linear behavior in dose response. The response curve was fit to the following second-order polynomial which was plotted as the solid line in FIG. 10:

$$\text{Signal(Volts)}=2.741\times10^{-4}\times\text{Dose(cGy)}-1.062\times10^{-7}\times\text{Dose}^2(cGy^2)$$

Figure 11:
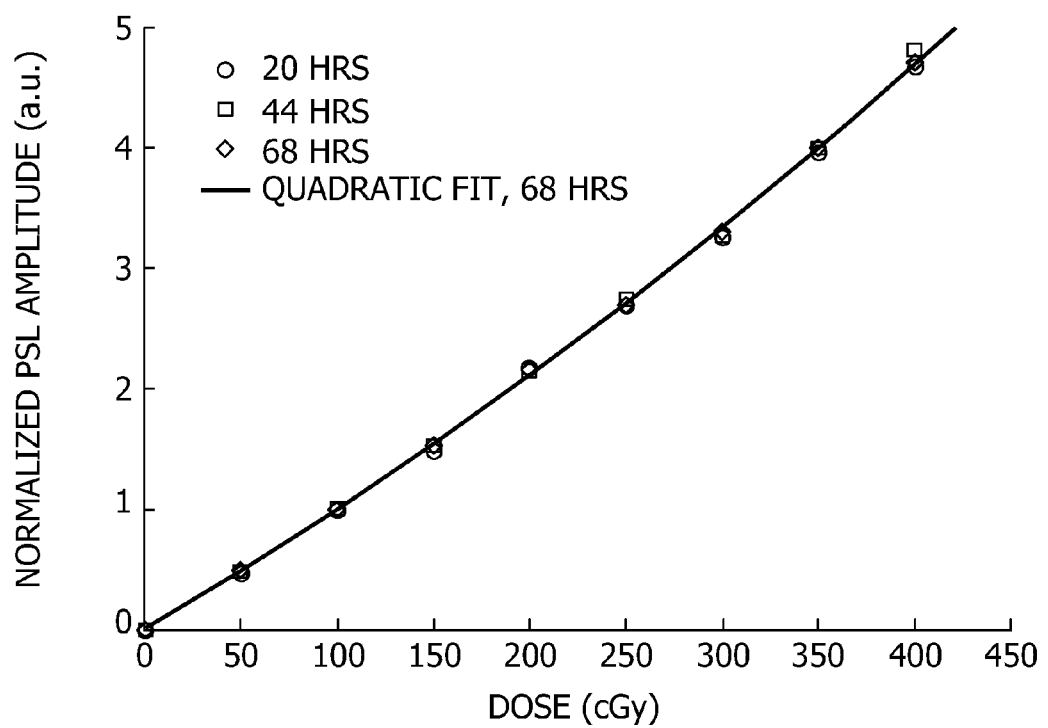
FIG. 11 graphically illustrates the response of dosimeters of FIG. 4 after an x-ray dose of 6 MV read at time delays of 20, 44 and 68 hours.

A fixed delay time of 20 hours between irradiation and reading was used. It was expected, however, that a difference in the delay time would not affect the readout results. FIG. 11 shows the measurements, normalized to the readings at 100 cGy, for a batch of 8 dosimeters exposed to a 6 MV beam up to 400 cGy and read at different delay times of 20, 44 and 68 hours. As the delay time increased, the PSL signal decreased following the fading curve (FIG. 11); however, the normalized curves agreed with each other within the experimental uncertainty, indicating no delay time effect. Absolute doses can be deduced from readings at any delay time provided the fading characteristics are known.

Example 9

Beam Energy Dependence of the Dosimeters

For megavoltage x-ray beams, dosimeters were irradiated using 6 MV, 10 MV and 18 MV photons at a SSD of 90 cm, a depth of 10 cm and a field size of 20×20 $cm^2$. For the electron beams, the dosimeters were irradiated using 6 MeV, 9 MeV, 12 MeV, 16 MeV and 20 MeV electron beams with the dosimeters placed at the respective depths of maximum dose (dmax).

Figure 12:
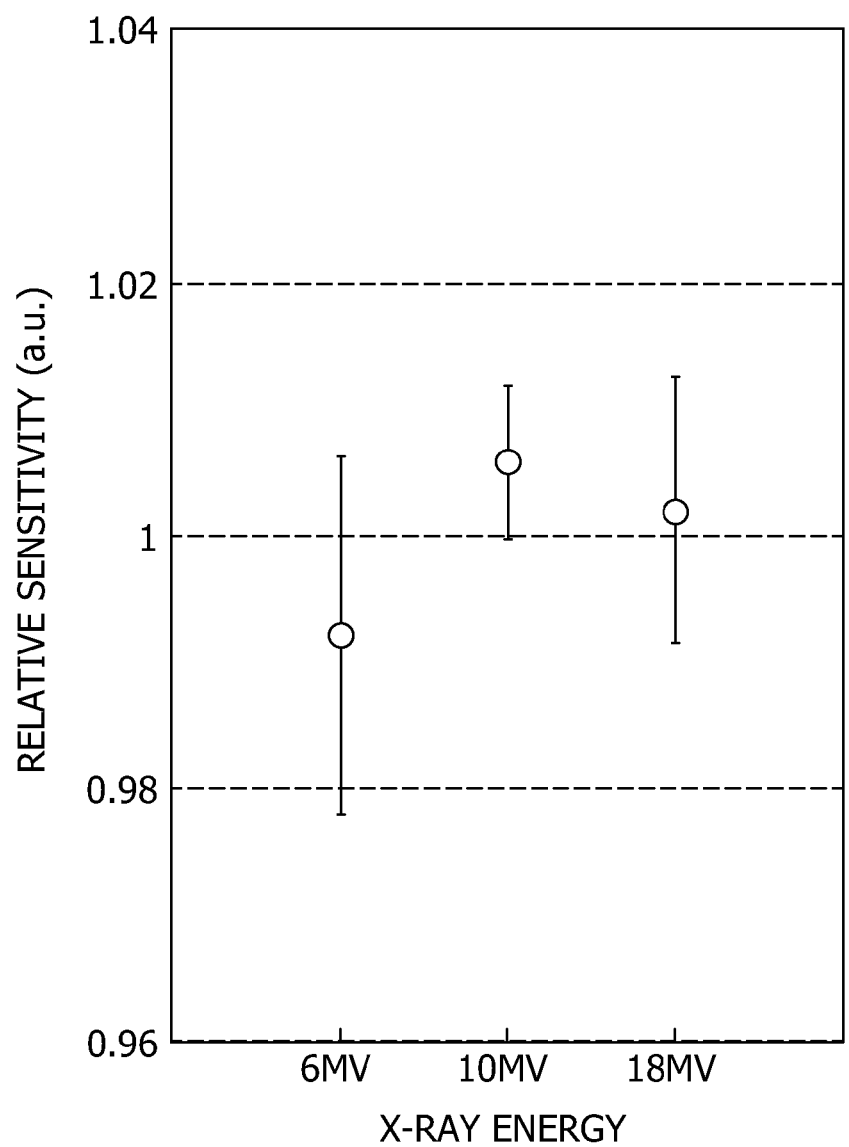
FIG. 12 graphically illustrates the sensitivity dependence of dosimeters of FIG. 4 to x-rays.
Figure 13:
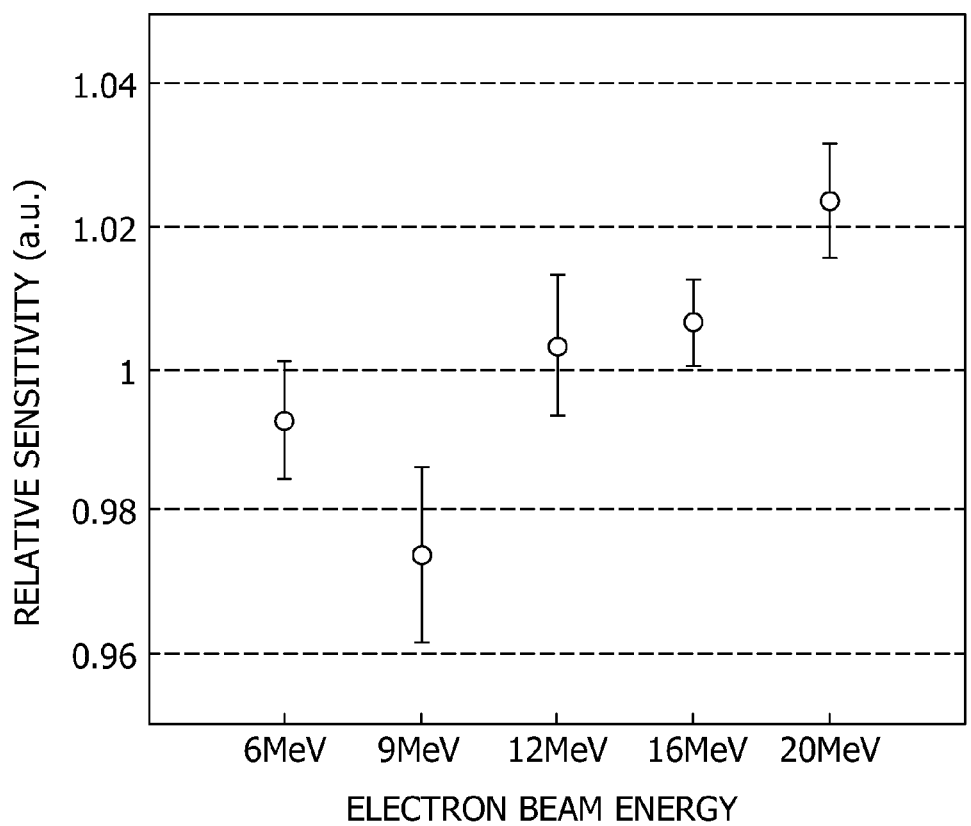
FIG. 13 graphically illustrates the sensitivity dependence of dosimeters of FIG. 4 to electron beams.

The sensitivity dependence on nominal incident beam energy for x-rays is illustrated in FIG. 12 and for electron beams in FIG. 13. Within a measurement uncertainty of +2.5%, the KCl:$Eu^{2+}$ dosimeters showed no energy dependence for either open field x-rays or megavoltage electrons commonly available from a multi-modality linear accelerator.

Example 10

Dose Rate Dependence of the Dosimeters

The dose rate dependence was investigated using a 6 MV beam. The dosimeters were placed at dmax (1.5 cm) with a field size of 10×10 cm² and a SSD of 100 cm. Nominal dose rates of 100, 200, 300, 400, 500 and 600 cGy/min (based on the same number of MU/min) were delivered by changing the accelerator repetition rate. A lower dose rate of 15 cGy/min was also delivered by irradiating the dosimeter underneath fully closed multileaf collimators (MLCs) and a higher dose rate of 1000 cGy/min was achieved by reducing the SSD to 77 cm. At each dose rate, a dose of 100 cGy was delivered to the dosimeter.

Figure 14:
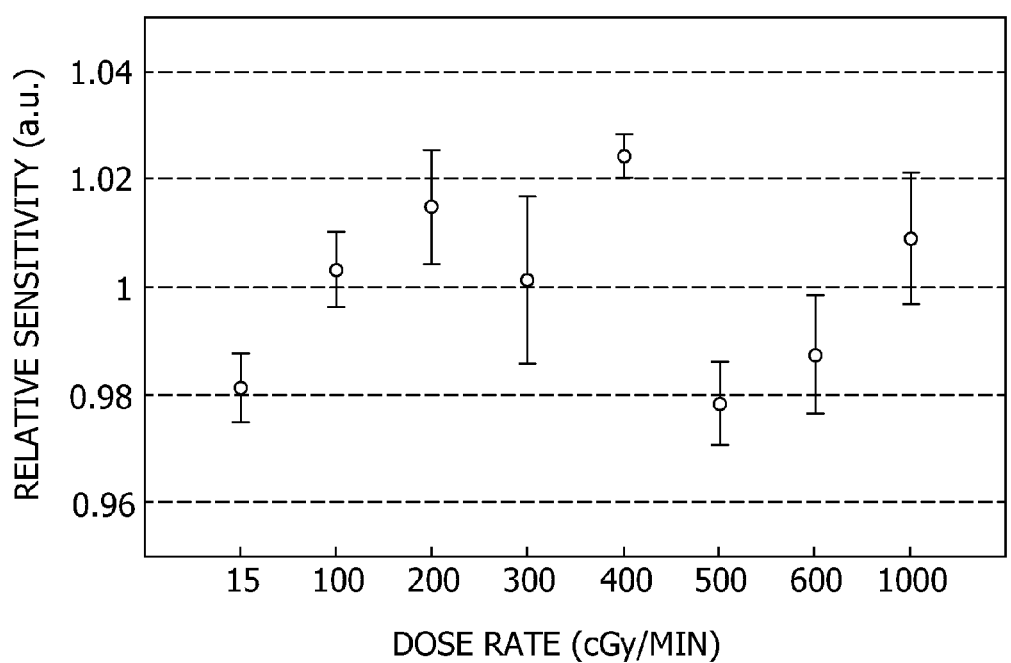
FIG. 14 graphically illustrates the sensitivity variations of the dosimeters of FIG. 4 as a function of dose rate after irradiation by a 6 MV beam.

FIG. 14 illustrates the sensitivity variations of the KCl:$Eu^{2+}$ dosimeters as a function of dose rate after irradiation by the 6 MV beam. There was no variation in sensitivity for dose rates ranging from 15 cGy/min (underneath a fully closed MLC) to 1000 cGy/min (at an SSD of 77 cm) within a measurement uncertainty of ±2.5%.

Example 11

Field Size and Depth Dependence of the Dosimeters

Varying field sizes and depths altered the incident fluence spectra, i.e., the scatter-to-primary x-ray ratios, at the dosimeter plane. The dosimeters were irradiated at isocenter to 200 cGy (SAD=100 cm) at four depths (5 cm to 20 cm) for each of five square field sizes (5×5 cm² to 25×25 cm²). A sensitometric curve for the dose range of 170 cGy to 250 cGy was obtained at a depth of 10 cm and a field size of 10×10 cm². The ratio of the measured dose using this calibration curve to the dose measured by an ionization chamber was used to indicate the magnitude of dose measurement error. For comparison, the measurements were repeated using Kodak XV, Kodak EDR2 radiographic films and the Agfa MD10 (Eastman Kodak, Rochester, N.Y.) CR plate. The films were processed using a diagnostic quality film processor (Kodak RP X-Omat Processor, Eastman Kodak Co., Rochester, N.Y.) and the optical densities were measured using a calibrated manual densitometer (Digital Densitometer II, Victoreen). The Agfa MD10 CR plate was made of $BaFBr_{0.85}I_{0.15}:Eu^{2+}$. Small (7 mm diameter) chips were cut from a CR plate. The chips were irradiated in the same manner as the KCl:$Eu^{2+}$ chips and read using the reader of Example 3.

Figure 15:
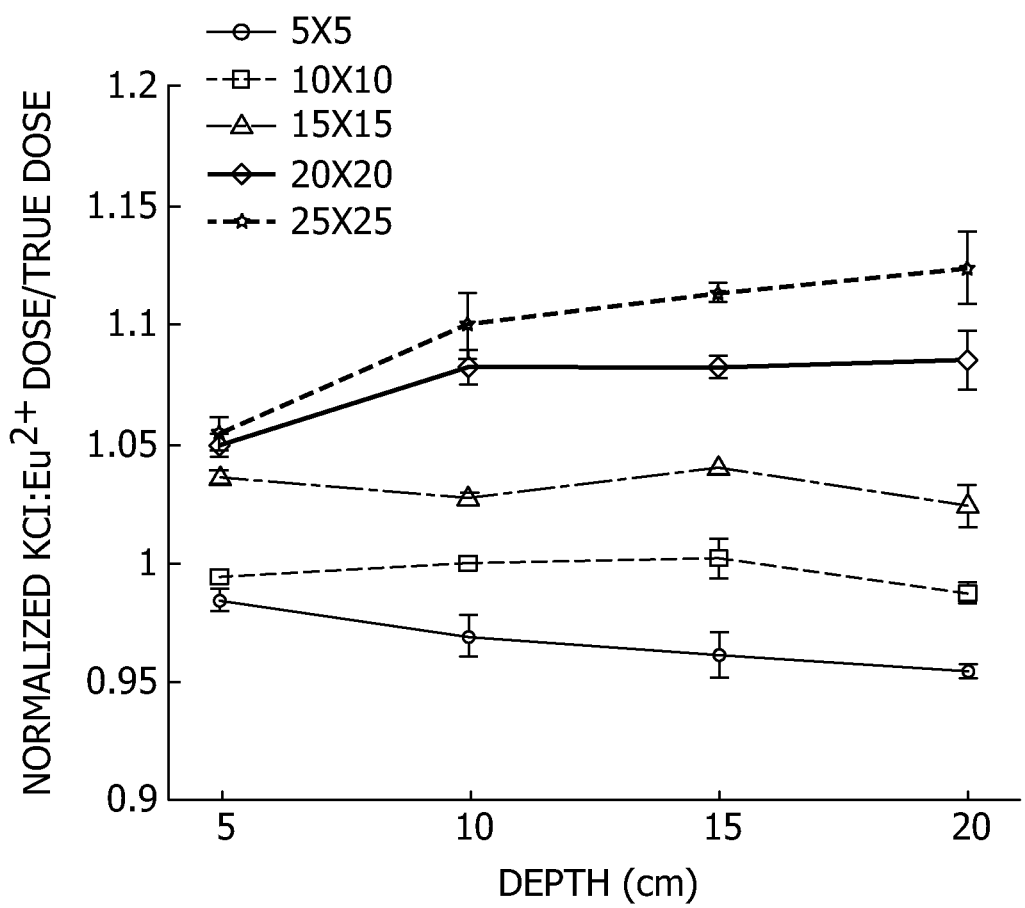
FIG. 15 graphically illustrates the relative sensitivities of the dosimeters of FIG. 4 after a 200 cGy dose (6 MV x-ray) at various field sizes and depths.

The effective atomic number for KCl:$Eu^{2+}$ material is 18 (since the amount of europium is on the order of ppm it has a negligible contribution to the effective Z). Due to the $Z^3$-dependence of the photoelectric mass attenuation coefficient, an over-response to low-energy scattered photons was expected for KCl:$Eu^{2+}$ dosimeters. This was evaluated by examining the dosimeters' responses to variations in field size and depth. These data are indicative of the effect of using a single dose response calibration curve for measurements with multiple effective field sizes and multiple depths. As the field size and depth increase, the scatter-to-primary dose ratio increases, so detectors that are oversensitive to low-energy photons will overestimate the dose at the portal center. FIG. 15 shows the relative sensitivities of KCl:$Eu^{2+}$ dosimeters that received a 200 cGy dose (6 MV x-ray) at various field sizes and depths. The results were normalized to the calibration conditions, i.e., at a depth of 10 cm in a 10×10 cm² field. As the field size and depth increased, the dosimeters' sensitivities increased due to the increase in the scatter-to-primary ratio. As a result, a maximum over-response of 12% was observed in the largest field and depth (25×25 cm² and 20 cm, respectively). As a comparison, EDR2 film exhibited less energy dependence (8%) although it had a larger effective Z of 43. For the commercially available $BaFBr_{0.85}I_{0.15}:Eu^{2+}$ CR plate, as much as 82% over-response was observed.

Example 12

Figure 16:
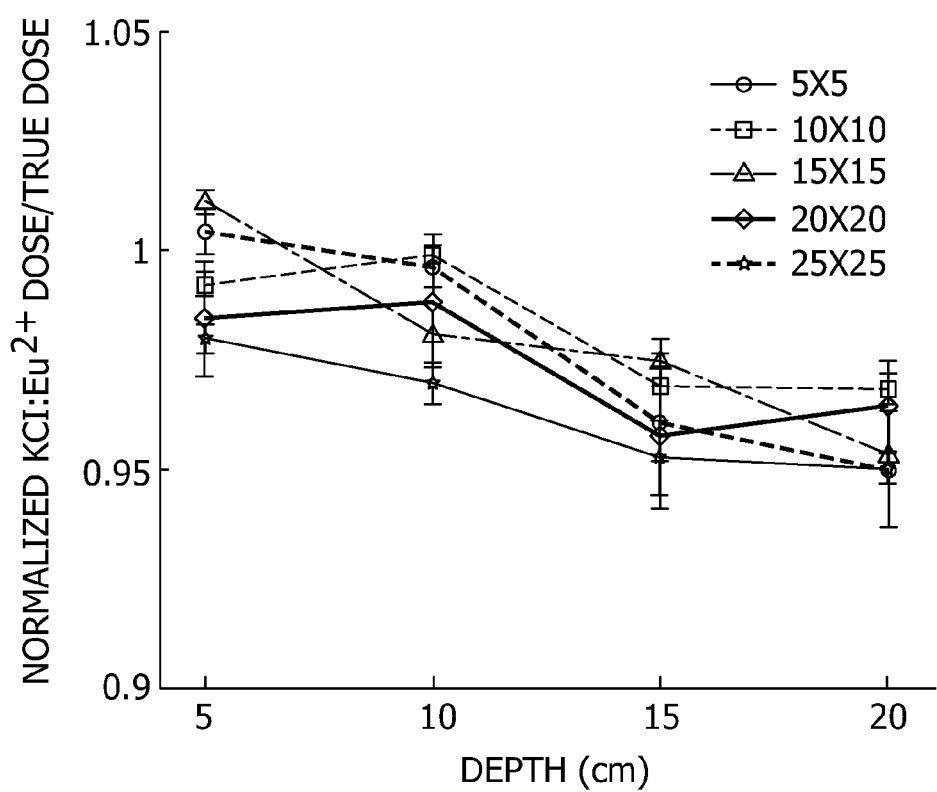
FIG. 16 graphically illustrates depth dependence of the dosimeters of FIG. 4 sandwiched between two lead foils separated by 6 mm solid water material upstream and 3 mm solid water material downstream.

Field Size and Depth Dependence of the Dosimeters with Low-Energy Photon Filters Field size and depth dependence measurements were repeated with two 0.3-mm-thick lead foils sandwiching the dosimeters, separated by 6 mm solid water material upstream and 3 mm downstream. As shown in FIG. 16, for all the field sizes the dosimeters showed weak depth dependence with an approximately 2% variation from 5 cm to 20 cm.

Example 13

Monte Carlo Simulated Dose Profiles for Dosimeters with Thin KCl:$Eu^{2+}$ Storage Phosphors Dose profiles for a 6 MV beam and a SSD of 100 cm were simulated using Monte Carlo simulations. Monte Carlo methods are an effective tool for the determination of clinical parameters in radiotherapy and radiation beam characterization. The methods include simulating the depth dose profile in a water phantom stricken by an x-ray beam. A Varian Linac was modeled in detail using BEAMnrcMP, a general purpose Monte Carlo simulation system based on the EGSnrcMP code system for modeling coupled electron and photon transport. The phase space file was used as the input source for Dosxyznrc to further simulate the 3D dose distribution in a solid water phantom with a size of 40×40×40 cm³. The typical voxel size is 0.5 cm×0.5 cm×10 μm for lateral dose profile simulation and 3 cm×3 cm×10 μm at central axis for PDD simulation. Up to 4×10⁸ histories were used to achieve good statistics for both BEAMnrcMP and DOSXYZnrc.

Figure 17:
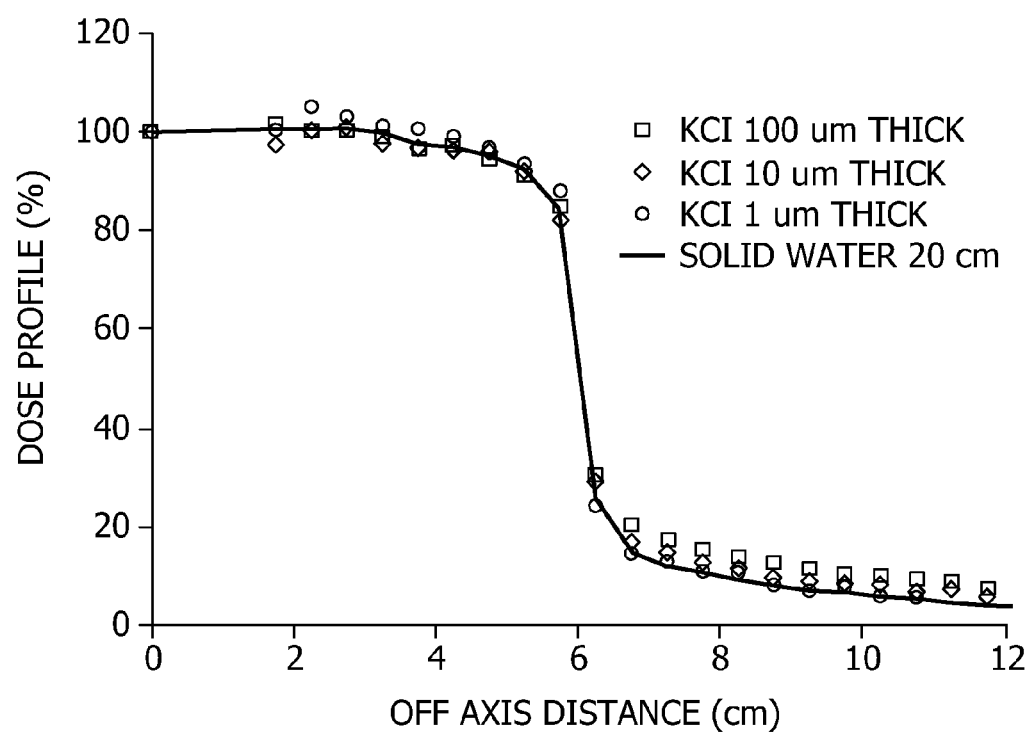
FIG. 17 graphically illustrates Monte Carlo simulations of KCl:Eu$^{2+}$ storage phosphors with thicknesses of 100 µm, 10 µm and 1 µm.

FIG. 17 illustrates simulations using KCl:$Eu^{2+}$ storage phosphors with thicknesses of 100 μm, 10 μm and 1 μm at a depth of 20 cm for a 10×10 cm² field size. As can be seen from FIG. 17, reducing the thickness of the phosphor creates a more water-like response.

Figure 18:
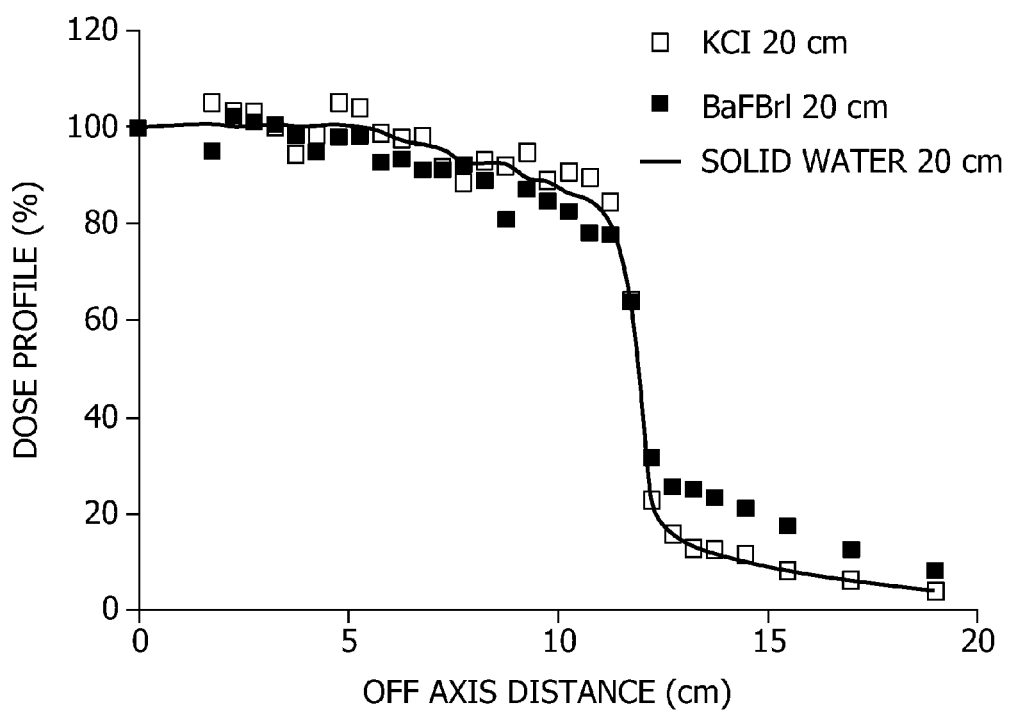
FIG. 18 graphically illustrates the Monte Carlo simulated dose profile of a 1 µm thick BaFBr$_{0.85}$I$_{0.15}$:Eu$^{2+}$ storage phosphor and a 1 µm thick KCl:Eu$^{2+}$ storage phosphor.

FIG. 18 illustrates a dose profile comparison between a 1 μm thick KCl:$Eu^{2+}$ storage phosphor and a 1 μm thick $BaFBr_{0.85}I_{0.15}:Eu^{2+}$ storage phosphor at a depth of 20 cm and a field size of 20×20 cm². As can be seen, the KCl:$Eu^{2+}$ storage phosphor has a more water-like response than the $BaFBr_{0.85}I_{0.15}:Eu^{2+}$ storage phosphor.

Figure 19:
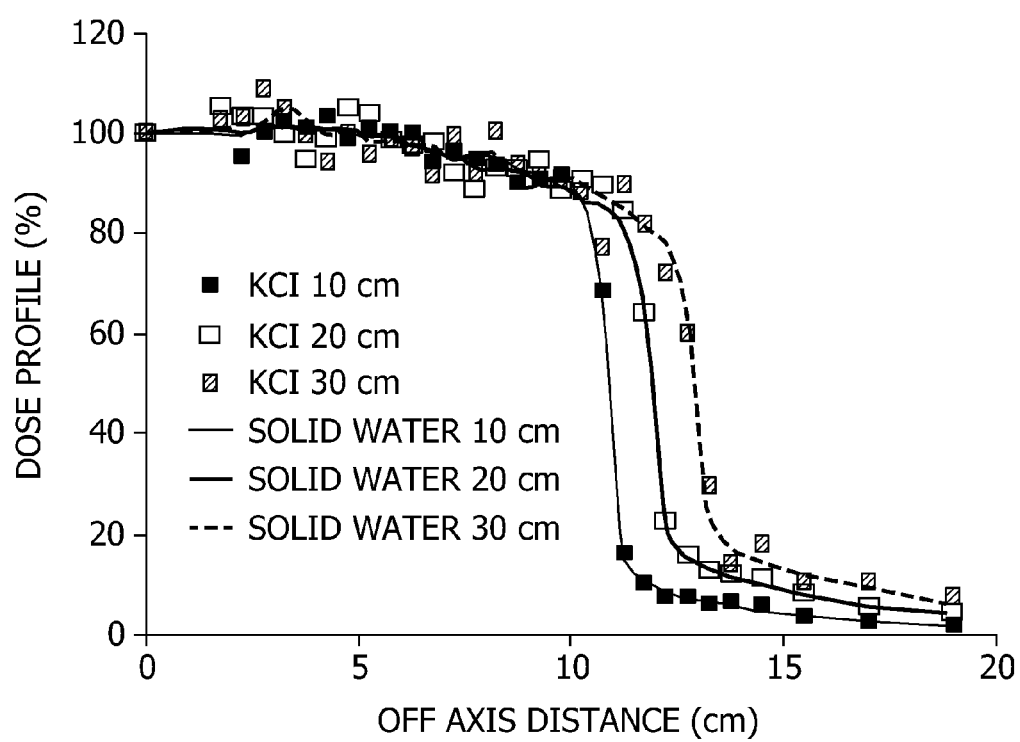
FIG. 19 graphically illustrates the Monte Carlo simulated dose profile for a 1 µm thick KCl:Eu$^{2+}$ storage phosphor at depths of 30 cm, 20 cm and 10 cm.

The simulated dose profiles for a 1 μm thick KCl:$Eu^{2+}$ storage phosphor at depths of 30 cm, 20 cm and 10 cm for a field size of 20×20 cm² is shown in FIG. 19. The 1 μm thick KCl:$Eu^{2+}$ storage phosphor has a water-like response profile at each depth.

Figure 20:
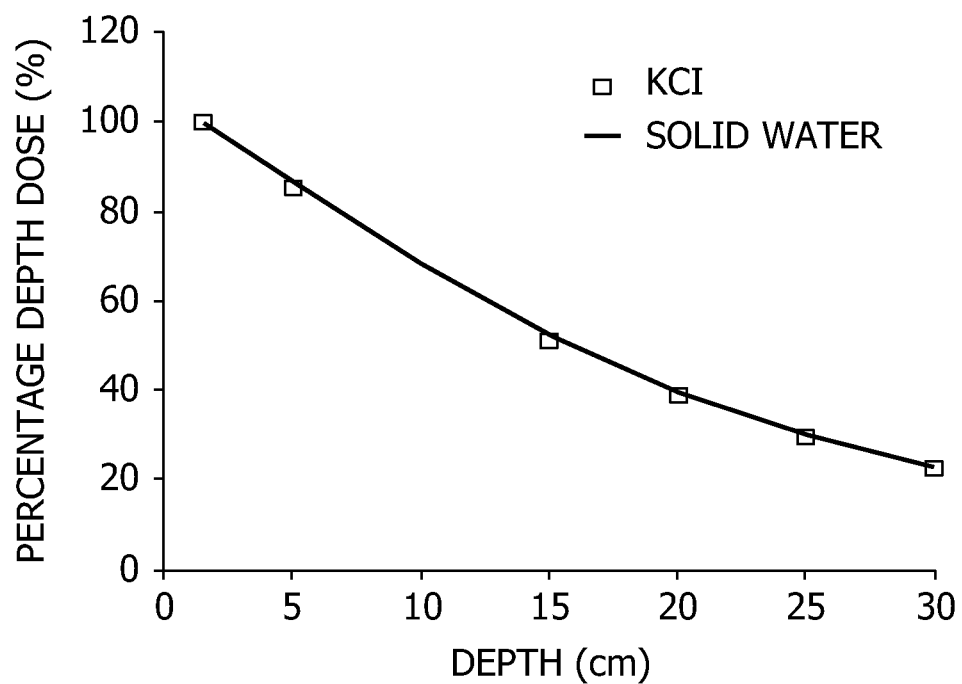
FIG. 20 graphically illustrates the Monte Carlo simulated depth dose for a 1 µm an thick KCl:Eu$^{2+}$ storage phosphor.

The simulated percentage depth dose for a 1 μm thick KCl:$Eu^{2+}$ storage phosphor for a field size of 20×20 cm² is shown in FIG. 20. The 1 μm thick KCl:$Eu^{2+}$ storage phosphor had a water-like response profile across the depth profile.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatus and methods without departing from the scope of the disclosure, it is intended that all matter contained in the above description and shown in the accompanying figures shall be interpreted as illustrative and not in a limiting sense.

What is claimed is:

1. A radiation dosimeter for measuring the dose of radiation applied during radiation therapy, the dosimeter comprising a storage phosphor, the storage phosphor having a europium-doped potassium chloride active layer with an effective thickness of less than about 10 μm.

2. A radiation dosimeter as set forth in claim 1 wherein the active layer has a thickness of less than about 3 μm.

3. A radiation dosimeter as set forth in claim 1 wherein the active layer has a thickness of less than about 1 μm.

4. A radiation dosimeter as set forth in claim 1 wherein the thickness of the active layer is about equal to the effective thickness of the active layer.

5. A radiation dosimeter as set forth in claim 1 wherein the storage phosphor contains at least about 50 ppm by weight europium.

6. A radiation dosimeter as set forth in claim 1 wherein the storage phosphor has a buffer layer and a plurality of active layers, each active layer having an effective thickness less than about 10 μm.

7. A radiation dosimeter as set forth in claim 1 wherein the active layer comprises binder material.

8. A method for measuring the amount of radiation applied from a source of radiation, the method comprising:
applying a dose of radiation in the direction of a dosimeter comprising a storage phosphor, the storage phosphor having a europium-doped potassium chloride active layer with an effective thickness of less than about 10 μm;
optically stimulating the storage phosphor to emit photons;
detecting emitted photons; and
generating a signal based on the amount of photons detected.

9. A method as set forth in claim 8 wherein the signal is used to calibrate the source of radiation.

10. A method as set forth in claim 8 wherein the signal is used to verify a radiation dose applied to cancerous tissue of a patient.

11. A method as set forth in claim 8 wherein the dose was applied to a cancerous tissue.

12. A method as set forth in claim 8 wherein the radiation is in the x-ray range and the x-ray voltage is at least about 1 MV.

13. A method as set forth in claim 8 comprising:
resetting the storage phosphor;
applying a second dose of radiation in the direction of the dosimeter;
optically stimulated the storage phosphor to emit photons after the second dose of radiation is applied; and
generating a second signal based on the amount of photons detected.

14. A method as set forth in claim 8 wherein the active layer has an effective thickness of less than about 3 μm.

15. A method as set forth in claim 8 wherein the active layer has an effective thickness of less than about 1 μm.

16. A method for treating a patient having a cancerous tumor, the method comprising;
applying a targeted dose of radiation to the cancerous tumor; and
verifying that the targeted dose of radiation was applied to the tumor by applying a dose of radiation in the direction of a dosimeter comprising a storage phosphor, the storage phosphor having a europium-doped potassium chloride active layer with an effective thickness of less than about 10 μm.

17. A method as set forth in claim 16 wherein the targeted dose of radiation applied to the cancerous tumor and the dose applied in the direction of the dosimeter are the same dose.

18. A method as set forth in claim 16 wherein the targeted dose of radiation applied to the cancerous tumor and the dose applied in the direction of the dosimeter are a different dose.

19. A method as set forth in claim 16 wherein the targeted dose is at least 1 Gy.

20. A method as set forth in claim 16 wherein the active layer has an effective thickness of less than about 1 μm.

* * * * *